US008372606B2

(12) United States Patent
Kishino et al.

(10) Patent No.: US 8,372,606 B2
(45) Date of Patent: Feb. 12, 2013

(54) METHODS FOR OBTAINING CRYSTALS OF A BASIC AMINO ACID HYDROCHLORIDE

(75) Inventors: Mitsuhiro Kishino, Saga (JP); Toshimichi Kamei, Kawasaki (JP)

(73) Assignee: Ajinomoto Co., Inc., Tokyo (JP)

( * ) Notice: Subject to any disclaimer, the term of this patent is extended or adjusted under 35 U.S.C. 154(b) by 494 days.

(21) Appl. No.: 12/491,341

(22) Filed: Jun. 25, 2009

(65) Prior Publication Data

US 2009/0291477 A1 Nov. 26, 2009

Related U.S. Application Data

(63) Continuation of application No. PCT/JP2007/070555, filed on Oct. 22, 2007.

(30) Foreign Application Priority Data

Dec. 25, 2006 (JP) .................................. 2006-347650

(51) Int. Cl.
C12P 13/24 (2006.01)

(52) U.S. Cl. ......... 435/107; 435/106; 435/114; 435/115

(58) Field of Classification Search .................. None
See application file for complete search history.

(56) References Cited

U.S. PATENT DOCUMENTS

| | | | |
|---|---|---|---|
| 3,871,960 A | 3/1975 | Kubota et al. | |
| 4,346,170 A | 8/1982 | Sano et al. | |
| 4,388,405 A | 6/1983 | Sano et al. | |
| 4,556,463 A * | 12/1985 | Minz et al. | 205/536 |
| 4,835,309 A | 5/1989 | Jaffari et al. | |
| 4,919,945 A | 4/1990 | Spindler et al. | |
| 5,312,980 A | 5/1994 | Yonsel et al. | |
| 5,756,761 A | 5/1998 | Dueppen et al. | |
| 5,814,513 A | 9/1998 | Tanabe et al. | |
| 6,258,554 B1 | 7/2001 | Ikeda et al. | |
| 6,329,548 B1 | 12/2001 | Hasegawa et al. | |
| 6,340,486 B1 | 1/2002 | Binder et al. | |
| 6,344,347 B1 | 2/2002 | Kino et al. | |
| 6,465,025 B2 | 10/2002 | Binder et al. | |
| 6,465,243 B2 | 10/2002 | Okada et al. | |
| 6,479,700 B2 | 11/2002 | Soper et al. | |
| 6,756,510 B1 | 6/2004 | Binder et al. | |
| 6,790,647 B2 | 9/2004 | Ptitsyn et al. | |
| 6,800,185 B2 | 10/2004 | Hasegawa et al. | |
| 6,874,444 B2 | 4/2005 | Peisker et al. | |
| 6,979,560 B1 | 12/2005 | Livshits et al. | |
| 7,169,586 B2 | 1/2007 | Ptitsyn et al. | |
| 7,211,416 B2 | 5/2007 | Asahara et | |
| 7,211,421 B2 | 5/2007 | Tsujimoto et al. | |
| 7,217,543 B2 | 5/2007 | Gunji et al. | |
| 7,220,570 B2 | 5/2007 | Usuda et al. | |
| 7,223,572 B1 | 5/2007 | Gunji et al. | |
| 7,335,506 B2 | 2/2008 | Gunji et al. | |
| 7,399,617 B1 | 7/2008 | Livshits et al. | |
| 7,416,740 B2 | 8/2008 | Kushiki et al. | |
| 7,439,038 B2 | 10/2008 | Gunji et al. | |
| 2002/0025564 A1 | 2/2002 | Kobayashi et al. | |
| 2002/0058315 A1 | 5/2002 | Lunts et al. | |
| 2003/0148475 A1 | 8/2003 | Ptitsyn et al. | |
| 2003/0165591 A1 | 9/2003 | Baricco et al. | |
| 2005/0026258 A1 | 2/2005 | Ptitsyn et al. | |
| 2007/0249017 A1 | 10/2007 | Usuda et al. | |
| 2008/0038825 A1 | 2/2008 | Gunji et al. | |
| 2008/0199919 A1 | 8/2008 | Gunji et al. | |
| 2009/0054685 A1 | 2/2009 | Murata et al. | |
| 2009/0104667 A1 | 4/2009 | Asakura et al. | |

FOREIGN PATENT DOCUMENTS

| | | |
|---|---|---|
| EP | 0 534 865 | 3/1993 |
| EP | 0 729 451 | 9/1996 |
| EP | 0770676 | 5/1997 |
| EP | 1 016 710 | 7/2000 |
| EP | 1016651 | 7/2000 |
| EP | 1062877 | 12/2000 |
| EP | 1106602 | 6/2001 |
| EP | 1 170 358 | 1/2002 |
| EP | 1 170 361 | 1/2002 |
| EP | 1752543 | 2/2007 |
| EP | 1813677 | 8/2007 |
| JP | 48-27476 | 4/1973 |
| JP | S48-27476 | 8/1973 |
| JP | 56-5099 | 1/1981 |

(Continued)

OTHER PUBLICATIONS

Eggeling et al., Biotechnology, 2006, 3$^{rd}$ edition, Cambridge University Press, Chapter 14, "Amino acids", p. 335-357.*

(Continued)

Primary Examiner — Kade Ariani
(74) Attorney, Agent, or Firm — Shelly Guest Cermak; Cermak Nakajima LLP

(57) ABSTRACT

The present invention provides a method for separating and obtaining a basic amino acid hydrochloride from a basic amino acid fermentation broth or an enzyme reaction solution which enzyme reaction is catalyzed by viable microbial cells which are able to produce a basic amino acid, each containing sulfate ions, wherein product yields and qualities are almost the same and are secured more easily, as compared with the conventional technique. The method may include the steps of adding a metal chloride such as calcium chloride, potassium chloride, magnesium chloride, and barium chloride to the basic amino acid fermentation broth or the enzyme reaction solution containing sulfate ions to precipitate the sulfate ions as crystals of the resulting metal sulfate, (2) removing the metal sulfate crystals from the basic amino acid solution, (3) cooling the basic amino acid fermentation broth or the enzyme reaction solution from which the metal sulfate crystals have been removed while maintaining the concentration of the metal sulfate below its saturation concentration, resulting in precipitatation the basic amino acid as hydrochloride crystals, and (4) separating and collecting the basic amino acid hydrochloride crystals.

4 Claims, No Drawings

FOREIGN PATENT DOCUMENTS

| | | |
|---|---|---|
| JP | 56-18596 | 2/1981 |
| JP | 2000189180 | 7/2000 |
| JP | 2001-25368 | 1/2001 |
| KR | 10-2002-0016544 | 3/2002 |
| KR | 10-2004-0049294 | 6/2004 |
| RU | 2003677 | 11/1993 |
| RU | 2 119 536 | 9/1998 |
| RU | 2 215 783 | 3/2003 |
| SU | 266649 | 3/1970 |
| SU | 1 518 948 | 4/1995 |
| WO | WO95/14002 | 5/1995 |
| WO | WO95/23864 | 9/1995 |
| WO | WO96/17930 | 6/1996 |
| WO | WO2005/010175 | 2/2005 |

OTHER PUBLICATIONS

Decision of Patent Grant for Korean Patent App. No. 2009-7014763 (Jun. 1, 2011).

International Search Report and Written Opinion of the International Searching Authority for PCT Patent App. No. PCT/JP2007/070555 (Nov. 13, 2007).

Decision on Grant of Patent for Invention for Russian Patent App. No. 2009124135/10(033446), issued on Mar. 5, 2012, with English translation thereof.

Supplementary European Search Report for EP Patent App. No. 07830289.0 (Nov. 23, 2012).

\* cited by examiner

METHODS FOR OBTAINING CRYSTALS OF A BASIC AMINO ACID HYDROCHLORIDE

This application is a continuation of PCT/JP2007/070555, filed Oct. 22, 2007, which claims priority under 35 U.S.C. §119 to Japanese Patent Application No. 2006-347650, filed on Dec. 25, 2006, both of which are incorporated by reference in their entireties.

BACKGROUND OF THE INVENTION

1. Field of the Invention

The present invention relates to a method for obtaining crystals of a basic amino acid hydrochloride from a basic amino acid fermentation broth or an enzyme reaction solution which enzyme reaction has been catalyzed with viable cells of a basic amino acid-producing microorganism, wherein the broth or the solution contains sulfate ions.

2. Brief Description of the Related Art

Basic amino acid fermentation broths and enzyme reaction solutions typically contain sulfate ions which are derived from the ammonium sulfate which is present as a nitrogen source in either the fermentation media or substrate solutions for the enzyme reaction.

Conventionally, in order to obtain crystals of a basic amino acid hydrochloride from such a basic amino acid fermentation broth or an enzyme reaction solution, which broth or solution contains sulfate ions, at a high purity, first, the basic amino acid fermentation broth or the enzyme reaction solution is passed through an ammonium-type cation exchange resin column. The basic amino acids are adsorbed onto the resin, while the sulfate ions are removed in the form of an ammonium sulfate solution together with the exchanged or desorbed ammonium ions. Thereafter, the ion exchange resin on which the basic amino acids have been adsorbed is washed with an ammonia solution to elute the basic amino acids, and the basic amino acids are then concentrated as the free form in the eluate. Finally, the free basic amino acid that is obtained is neutralized with hydrochloric acid, whereby basic amino acid hydrochloride crystals are formed and obtained from the mother liquor.

However, this method can be problematic in the following respects. Namely, (1) the eluted ammonium sulfate solution must be concentrated using an enormous amount of vapor so that the byproduct of ammonium sulfate can be recycled, and (2) a large amount of waste water is discharged when the resin is washed.

Other methods for obtaining a basic amino acid include, for example, a method wherein a lysine fermentation broth is supplied with a potassium hydroxide solution to crystallize the lysine base (free form) (European Patent Publication No. 0534865), and a method wherein a lysine fermentation broth is filtered through activated carbon to remove the cells of the chosen lysine-producing microorganism, then the resulting filtrate is mixed with a calcium hydroxide solution which serves to deposit and remove the calcium sulfate which is generated, and finally the remainder is concentrated to remove the ammonia, and the lysine base is obtained (Russian Patent Publication No. 183581). Then, the lysine base is mixed with hydrochloric acid, whereby lysine hydrochloride crystals are obtained.

However, the methods described above wherein an expensive metal hydroxide and hydrochloric acid are used as auxiliary materials and the resulting by-product metal sulfate is very cheap compared with the metal per se, result in a manufacturing procedure wherein the costs for the auxiliary materials are high. Furthermore, after mixing with a metal hydroxide, the solution is concentrated to a pre-determined lysine concentration by using heat at a high pH, which results in degradation of the lysine.

Moreover, these methods involve a suspension which contains metal sulfate crystals and a basic amino acid. However, the basic amino acid is in the free base form in the suspension, and therefore, the suspension is viscous and it is difficult to separate the metal sulfate crystals from the basic amino acid. As a result, a large amount of the amino acid adheres to the metal sulfate crystals to be discharged, resulting in a lower recovery rate of the amino acid of interest.

Exemplary methods of the present invention involve a suspension which contains the amino acid in the hydrochloride form and thus is not very viscous, which allows for easy separation of the metal sulfate crystals from the amino acid moiety and increases the recovery rate of the amino acid.

In addition, other problems exist, such as the metal hydroxide in aqueous solution is usually added at a concentration of not more than 50% which results in a decrease in the amino acid concentration in the system. This raises the cost for producing the vapor. 100% of metal hydroxide powder may be added to the system, but to do so is dangerous and difficult; and in addition, the separate required steps of adding the metal hydroxide and the hydrochloric acid complicates the production operation.

Previously, a metal chloride was not thought to react with a basic amino acid sulfate in a basic amino acid fermentation broth because it was believed that no anion exchange reaction occurs between the basic amino acid sulfate and the metal chloride. Namely, it was thought to be impossible that an equilibrium reaction would occur between the salts because the system consists of the basic amino acid sulfate in the solution phase and the metal chloride in the solid phase. It was believed that, in such a solid-liquid system, even if the metal chloride is added as a solid, the metal chloride would remain as a solid, while the dissolved basic amino acid sulfate would stay dissolved.

The amount of basic amino acids produced is not limited as long as they are generated by fermentation or by enzymatic methods using microbial cells as a catalyst. These amino acids include, for example, arginine, histidine and lysine. The form of the amino acids is not limited, but an L-form is one example.

Exemplary microbes according to the present invention include those which are able to produce the target amino acid or those which are able to catalyze the reaction to produce the target amino acid from substrates. The former are used in fermentation methods while the latter are used in enzymatic methods. As microbes, any bacteria, yeasts, filamentous bacteria and the like may be used, bacteria being one example. Bacteria may either be Gram-negative or Gram-positive. The microbe may be used alone or in combination with one or more other microbes.

L-lysine producing bacteria and methods for breeding the same are known, including those disclosed in, for example, WO 95/23864, WO 96/17930, WO 2005/010175, Japanese Patent Application Laid-Open (Kokai) Sho No. 56-18596, U.S. Pat. No. 4,346,170, and Japanese Patent Application Laid-Open (Kokai) No. 2000-189180. L-arginine producing bacteria and methods for breeding the same are also known, and include those disclosed in, for example, United States Patent Application Publication No. 2002/058315A1, Russian Patent Application No. 2001112869, EP 1170358A1 and EP 1170361A1. L-histidine producing bacteria and methods for breeding the same are also know, and include those disclosed in, for example, Russian Patent Nos. 2003677 and 2119536, U.S. Pat. Nos. 4,388,405, 6,344,347 and 6,258,554, Russian Patent Nos. 2003677 and 2119536, Japanese Patent Application Laid-Open (Kokai) Sho No. 56-005099 and EP1016710A. The same is the case with known L-ornithine producing bacteria and methods for breeding the same.

SUMMARY OF THE INVENTION

It is an aspect of the present invention to provide a method for separating and obtaining a basic amino acid hydrochloride from a basic amino acid fermentation broth or an enzyme reaction solution which enzyme reaction is catalyzed by viable microbial cells which are able to produce a basic amino acid, wherein the broth or the reaction solution contain sulfate ions. The product yields and qualities are almost the same and are obtained more easily as compared with conventional techniques. Hereinafter, unless otherwise indicated or unless a technically different interpretation is required, the description relating to the fermentation broth shall be also applicable to that for the enzyme reaction solution.

The present inventors have strenuously studied how to achieve the above aspects and found that the crystals of a basic amino acid hydrochloride can be obtained in a high yield and quality by a method wherein a metal chloride is added to a basic amino acid fermentation broth containing sulfate ions to precipitate the sulfate ions as metal sulfate crystals, which crystals are then separated to obtain a solution, followed by cooling the solution to precipitate the basic amino acid as its hydrochloride crystals.

Accordingly, the present invention includes the following aspects:

It is an aspect of the present invention to provide a method for obtaining the crystals of a basic amino acid hydrochloride from a basic amino acid fermentation broth or an enzyme reaction solution, which said enzyme reaction is catalyzed with viable microbial cells which are able to produce a basic amino acid, wherein the broth or the solution contains sulfate ions, comprising:

(1) adding a metal chloride selected from the group consisting of calcium chloride, potassium chloride, magnesium chloride, and barium chloride to the basic amino acid fermentation broth or the enzyme reaction solution, (2) precipating the resulting metal sulfate crystals, (3) removing the metal sulfate crystals from the basic amino acid fermentation broth or the enzyme reaction solution, (4) cooling the basic amino acid fermentation broth or the enzyme reaction solution from which the metal sulfate crystals have been removed while maintaining the concentration of the metal sulfate lower than its saturation concentration, (5) precipitating the basic amino acid in the form of its hydrochloride crystals, and (6) separating basic amino acid hydrochloride crystals, (7) collecting the basic amino acid hydrochloride crystals.

It is a further aspect of the present invention to provide the method as described above, wherein the microbial cells are removed before step (1) or after the step (3).

It is a further aspect of the present invention to provide the method as described above, wherein the basic amino acid is selected from the group consisting of arginine, lysine, ornithine, and histidine.

It is a further aspect of the present invention to provide the method as described above, wherein the basic amino acid fermentation broth or the enzyme reaction solution comprises a sulfate ion to basic amino acid ratio of 50 to 150%.

It is a further aspect of the present invention to provide the method as described above, wherein the metal chloride is added in a ratio of 80 to 120% relative to the sulfate ion.

Superior yields of high quality of a basic amino acid hydrochloride from a basic amino acid fermentation broth which contains sulfate ions by an extremely simple method.

DESCRIPTION OF THE PREFERRED EMBODIMENTS

To obtain crystals of a basic amino acid hydrochloride from a basic amino acid fermentation broth containing sulfate ions, first a metal chloride such as calcium chloride, potassium chloride, magnesium chloride, or barium chloride is added to the fermentation broth to precipitate the sulfate ions as crystals of the resulting metal sulfate.

The basic amino acid fermentation broth should necessarily contain sulfate ions at a concentration of an equivalent ratio of 50 to 150%, and in another example, 90 to 110%, relative to the basic amino acid. This is because if the equivalent ratio is over 150%, the amount of chloride ions necessary to cause the reaction must be increased while, if the equivalent ratio is less than 50%, the basic amino acid may be degraded due to a pH of over 8.5.

The basic amino acid can be arginine, lysine, ornithine, histidine, or a derivative thereof, and further it can either be in an optically active form, for example, the L- or D-form, or the racemic form.

In the fermentation broth or the enzyme reaction solution, the primary counterions to the basic amino acid are sulfate ions. Furthermore, the fermentation broth may contain crystals of the basic amino acid which are produced by the fermentation. In such a case, the broth must be subjected to an exemplary method of the present invention after removal or dissolution of the crystals.

The conditions under which a metal chloride is added to precipitate the metal sulfate crystals are as follows. The metal chloride can be selected as appropriate from the group of calcium, potassium, magnesium and barium chlorides and hydrates thereof. Of these, calcium and potassium chlorides generate a byproduct which can be used as a fertilizer, and so this is particularly advantageous.

The amount of the metal chloride to be added depends on the amount of the sulfate ions which are present, and can be an equivalent ratio of 80 to 120%, and in another example, 90 to 100%, relative to the sulfate ions.

The microbial cells in the basic amino acid fermentation broth may either be removed beforehand or not. However, in one example, the microbial cells can be removed beforehand to improve the separability of the resulting metal sulfate crystals.

Furthermore, the basic amino acid fermentation broth may either be concentrated or not before the metal chloride is added. If the broth is concentrated, the metal chloride can be added before the broth is concentrated for ease of operation. This is because when metal sulfate crystals with low solubility are used and are to be precipitated, a large supersaturation causes an extremely high slurry concentration, and the crystals are difficult to separate. One exemplary method is to add the metal chloride to the broth, separate the resulting metal sulfate crystals from the remainder, and then concentrate the mother liquor.

Potassium chloride may be added either before or after the broth is concentrated. However, when calcium chloride is employed, the operations become complicated because it is necessary to repeat the crystallization/separation steps, that is, because calcium chloride is added to the broth first, then the resulting calcium sulfate crystals are separated, the mother liquor is concentrated, and the newly resulting calcium sulfate crystals are separated.

The metal chloride can be added to the basic amino acid fermentation broth at a pH of 3 to 8.5 and at a temperature of 20 to 90° C. Specifically, the calcium chloride can be added to the broth at a pH of 3 to 8.5 and at a temperature of 20 to 90° C. Metal chlorides other than calcium chloride can be added to the broth at a pH of 3 to 8.5 and at a temperature of 50 to 90° C. This is because a pH of the broth over 8.5 causes degradation of the basic amino acid and decreases the recovery rate, while a pH of the broth lower than 3 increases the solubility of the basic amino acid, and results in a decreased recovery rate. In this case, an alkali is added to suppress the solubility, and results in an increased cost. When a metal chloride is used in an amount defined above, the broth is usually in a pH range as defined above, but an acid or alkali may be added to the broth, if necessary, to adjust the pH appropriately. Furthermore, when a metal chloride other than calcium chloride is added to the broth at a temperature lower than 50° C., the broth cannot be concentrated to prevent the basic amino acid from being precipitated, making it difficult at the later process stage to get a high crystallization rate. Meanwhile, a temperature over 90° C. degrades the amino acid.

Upon the crystallization of the metal sulfate, in the case of a solid-liquid anion exchange system wherein metal chloride crystals are present, a sufficient reaction time such as two hours or more, or in another example, ten hours or more, should be allowed after the addition of the metal chloride. In the case of a complete solution system, a more typical time is needed for the metal sulfate to be concentrated and crystallized.

Next, the metal sulfate crystals are removed from the basic amino acid fermentation broth. Various types of centrifuges are available to remove the metal sulfate crystals, and are not particularly limited. An SDC (Superdecanter-type separator) is one example because it is easy to maintain the temperature of the mother liquor.

Subsequently, the basic amino acid fermentation broth from which the metal sulfate crystals are removed is cooled to crystallize the basic amino acid hydrochloride, while maintaining the concentration of the metal sulfate below the saturation solubility of the metal sulfate. Before or after the fermentation broth is cooled to crystallize the basic amino acid hydrochloride, the fermentation broth may be concentrated, if necessary.

The concentration of the metal sulfate in the basic amino acid fermentation broth is necessarily kept to be below the saturation solubility of the metal sulfate while the fermentation broth is cooled to crystallize the basic amino acid hydrochloride. For this purpose, it is important that the saturation solubility of the metal sulfate in the basic amino acid fermentation broth is known in advance. For example, the respective solubilities of potassium sulfate and calcium sulfate are 10 g/dl and 0.05 g/dl at pH 5.5 and at 20° C. in a solution of any one of arginine, lysine, ornithine, and histidine. A person skilled in the art can easily determine suitable conditions for a given case by a preliminary test. Exemplary method of the present invention control the concentration to crystallize or cooling to crystallize so that the solution does not reach the saturation solubility of the metal sulfate.

Then, the precipitated crystals of the basic amino acid hydrochloride are separated. The crystals are separated in a manner similar to that in the above-described method wherein the metal sulfate crystals are removed from the basic amino acid fermentation broth, except that a superior centrifugation apparatus, such as a basket-type centrifuge, or the like, is appropriately used. This is because different from the above-described case where the metal sulfate crystals are separated from the basic amino acid fermentation broth, it is more important that the apparatus be used to clear the adherent mother liquor as much as possible, and then the product purity of the basic amino acid can be improved.

The crystals of the basic amino acid hydrochloride thus obtained are comparable in yield and quality to those obtained by conventional methods. Specifically, when potassium chloride is added to the arginine fermentation broth, a recovery rate of as low as less than 50% is obtained on the first cycle. But when the mother liquor which contains impurities is the starting broth, and then concentrated and partly transferred for the next cycle of the fermentation broth from which the microbial cells have been separated, to reuse such that the yield is maintained, a recovery of the product with a final purity of 99% in a final yield of 90% is obtained. When calcium chloride is added to an arginine fermentation broth and treated similarly, a final purity of 95% in a final yield of 90% is obtained. Further, when potassium chloride is added to a lysine fermentation broth and treated similarly, a purity of 99% in a yield of 90% is obtained. When calcium chloride is added to a lysine fermentation broth and treated similarly, a purity of 99% in a yield of 90% is obtained.

EXAMPLES

The present invention will be described in detail below with reference to the following non-limiting Examples and Comparative examples.

Example 1

Production of Lysine Hydrochloride Crystals (KCl)

Production of a lysine fermentation broth containing sulfate ions (lysine sulfate fermentation broth): A carbon source, a nitrogen source, and trace nutrients are dissolved in water, thermally sterilized, and then poured into a fermenter. A suspension of a previously proliferating lysine-producing microorganism is added to start the culture. The fermentation temperature is controlled using cold water to between 35 and 40° C., while air is supplied to the fermenter to control the level of dissolved oxygen. The broth can be produced by a well-known method, wherein the culturing is continued for about 25 to 40 hours until the production rate of the lysine decreases in the culture medium, and the medium is being supplemented with a carbon source, a nitrogen source, and a certain amount of nutrients when levels of these become insufficient during culturing.

The microbial cells were removed from the lysine sulfate fermentation broth which was obtained by the above-described method to give a microbial cell-free solution having the following composition.

TABLE 1

| Volume | 2,384 ml | 2,549 g |
|---|---|---|
| Lysine base | 10.9 w/w % | 279 g |
| $SO_4$ | 4.1 w/w % | 105 g |
| K | 0 w/w % | 1 g |
| Cl | 0.1 w/w % | 3 g |
| pH | 7.0 | |

This microbial cell-free solution was concentrated under vacuum (50 mmHg) to a 37 w/w % concentration in terms of lysine base (free form lysine), supplied with 142 g of potassium chloride (KCl), and stirred for 3 hours at 60° C. Then, the suspension was, using a table separator, separated into 135 g of wet crystals of the potassium sulfate ($K_2SO_4$) and 729 g of lysine hydrochloride solution. 258 g of water was added to this solution to maintain a temperature of 60° C. and prevent the precipitation of potassium sulfate, and then cooled in a 20° C. bath over a period of 6 hours down to 20° C. 10 g of lysine hydrochloride dihydrate crystals (seed crystals) were added to the solution to induce crystallization at 40° C. during the course of cooling. The cooled solution was centrifuged with a table-centrifuge to give 76 g of lysine hydrochloride dihydrate crystals, which were then dried for 30 minutes at 110° C. with a fluidized bed dryer to obtain 61 g of lysine hydrochloride anhydride crystals having a purity of 99%, the mother liquor being in an amount of 770 g.

On the other hand, further lysine hydrochloride anhydride crystals were obtained by a method wherein the mother liquor from a lysine fermentation broth is recycled as follows. 760 g of the final mother liquor was mixed with 1,947 g of a microbial cell-free fermentation solution containing 202 g of lysine (in the form of lysine hydrochloride) for the next cycle, 116 g of potassium chloride was added, and then concentrated to give a lysine concentration of 130 g/100 g-$H_2O$. The suspension resulting from this concentration was separated into 137 g of potassium sulfate and 890 g of a supernatant, and maintained at a temperature of 60° C. 160 g of water was added to the supernatant, and then cooled from 60° C. to 20° C. to obtain 215 g of wet crystals of lysine hydrochloride dihydrate, which were then dried at 110° C. for 30 minutes to obtain 180 g of lysine hydrochloride anhydride crystals having a purity of 99%.

This cycle was repeated nine times to obtain lysine hydrochloride anhydride crystals having a purity of 99% at a recovery rate of 90%.

Example 2

Production of Lysine Hydrochloride Crystals ($CaCl_2$ used)

A lysine sulfate fermentation broth was produced in the same way as described in Example 1. Sulfuric acid was used to adjust the pH of the fermentation broth to 3.0 for storage. The microbial cells in the lysine sulfate fermentation broth were removed with an MF membrane to obtain a microbial cell-free solution having the following composition.

TABLE 2

| Volume | 1,500 ml | 1,628 g |
|---|---|---|
| Lysine base | 10.7 w/w % | 175 g |
| $SO_4$ | 5.5 w/w % | 82 g |
| K | 0 w/w % | 0 g |
| Cl | 0.1 w/w % | 0 g |
| pH | 3.0 | |

12 g of calcium hydroxide ($Ca(OH)_2$) was added to the microbial cell-free solution to neutralize it to a pH of 5.5, and then it was stirred at 25° C. for 30 minutes to precipitate calcium sulfate crystals. The resulting suspension was filtered with a Nutsche funnel to obtain 9.8 g of calcium sulfate crystals. 114 g of calcium chloride ($CaCl_2$) was added to the filtrate, and calcium sulfate was precipitated. The suspension was filtered by the Nutsche funnel to obtain 231 g of wet crystals of calcium sulfate dihydrate and 1,475 g of a lysine hydrochloride solution. The solution was concentrated in a vacuum to 370 g, whereby a 60° C. aqueous concentrate of lysine hydrochloride (concentration: 35 g/dl) was obtained. This concentrate was cooled to 20° C. to obtain a suspension of lysine hydrochloride. Then, the suspension was separated with a table separator, but it is better if a large amount of wet crystals of calcium sulfate dihydrate are not included in the suspension. Consequently, the concentrate is filtered by the Nutsche funnel to obtain wet crystals of calcium sulfate and a lysine hydrochloride solution. The lysine hydrochloride solution is cooled to 20° C. to obtain a suspension of lysine hydrochloride. Then the suspension is separated with a table separator and thus 203 g of wet crystals of lysine hydrochloride dihydrate is obtained. Furthermore, the wet crystals are dried at 110° C. for 30 minutes with a fluid dryer to obtain 156 g of lysine hydrochloride anhydride crystals having a purity of 99%.

Furthermore, the lysine fermentation mother liquor is recycled, and the crystals of lysine hydrochloride anhydride are obtained in the same way as in Example 1. This cycle is repeated nine times to obtain crystals of lysine hydrochloride anhydride having a purity of 99% at a recovery rate of 90%.

Example 3

Production of Arginine Hydrochloride Crystals (KCl used)

Production of an arginine fermentation broth (arginine sulfate-containing fermentation broth) containing sulfate ions: An arginine sulfate fermentation broth can be produced in the same manner as in Example 1, except that a microorganism which produces arginine is used instead of the lysine-producing microorganism.

The microbial cells were removed from the arginine sulfate fermentation broth which was obtained by the above-described method to obtain a microbial cell-free solution having the following composition.

TABLE 3

| Volume | | 228 g |
|---|---|---|
| Arginine | 44 w/w % | 100 g |
| $SO_4$ | 12 w/w % | 27 g |
| pH | 6.5 | |

42 g of potassium chloride was added to this microbial cell-free solution, dissolved, and then concentrated to an arginine concentration of 100 g/100 g-$H_2O$. The 60° C. suspension was separated using a table separator into 40 g of wet crystals of potassium sulfate and 230 g of an arginine solution. Then, 30 g of water were added to this solution, cooled to 20° C., and then the resulting suspension was separated using a table separator into 30 g of wet crystals of arginine hydrochloride and 226 g of an arginine solution.

Furthermore, arginine hydrochloride crystals were obtained using a method wherein the arginine fermentation mother liquor was recycled. The cycle was repeated nine times to obtain an arginine hydrochloride crystals having a purity of 99% at a recovery rate of 90%.

Industrial Applicability

The present invention can be used in the fields of forage, cosmetic materials, and pharmaceutical materials using a basic amino acid hydrochloride.

The invention claimed is:

1. A method for obtaining the crystals of a basic amino acid hydrochloride from a fermentation broth containing the basic amino acid or an enzyme reaction solution containing the basic amino acid, said enzyme reaction is catalyzed by viable microbial cells producing the basic amino acid, and wherein the broth or the solution contains sulfate ions, the method comprising:

(1) adding a metal chloride selected from the group consisting of calcium chloride, potassium chloride, magnesium chloride, and barium chloride to the fermentation broth containing the basic amino acid and sulfate ions or the enzyme reaction solution containing the basic amino acid and sulfate ions at pH of 3 to 8.5 and temperature of 20 to 90° C., thereby precipitating the sulfate ions as metal sulfate crystals, wherein the fermentation broth or the enzyme reaction solution comprises sulfate ions at a concentration of an equivalent ratio of 50 to 150% relative to the basic amino acid, (2) removing said metal sulfate crystals from said fermentation broth or the enzyme reaction solution, (3) cooling the fermentation broth or the enzyme reaction solution from which the metal sulfate crystals have been removed while maintaining the concentration of the metal sulfate below its saturation concentration, (4) precipitating the basic amino acid in the form of hydrochloride crystals, (5) separating basic amino acid hydrochloride crystals, and (6) collecting the basic amino acid hydrochloride crystals.

2. The method as set forth in claim 1, wherein the microbial cells are removed before step (1) or after step (3).

3. The method as set forth in claim 1, wherein the basic amino acid is selected from the group consisting of arginine, lysine, ornithine, and histidine.

4. The method as set forth in claim 1, wherein the metal chloride is added in a ratio of 80 to 120% relative to the sulfate ion.

* * * * *